(12) United States Patent
Owen (10) Patent No.: US 11,559,595 B2
(45) Date of Patent: Jan. 24, 2023

(54) CURRENCY AND DOCUMENT SANITIZING APPARATUS AND SYSTEM

(71) Applicant: Dri Mark Products, Inc., Bethpage, NY (US)

(72) Inventor: Cathy Ann Owen, Bethpage, NY (US)

(73) Assignee: DRI MARK PRODUCTS, INC., Bethpage, NY (US)

( * ) Notice: Subject to any disclaimer, the term of this patent is extended or adjusted under 35 U.S.C. 154(b) by 22 days.

(21) Appl. No.: 17/381,977

(22) Filed: Jul. 21, 2021

(65) Prior Publication Data

US 2022/0062472 A1 Mar. 3, 2022

Related U.S. Application Data

(62) Division of application No. 17/319,990, filed on May 13, 2021, now Pat. No. 11,369,706.

(60) Provisional application No. 63/073,093, filed on Sep. 1, 2020.

(51) Int. Cl.
*A61L 2/10* (2006.01)
*A61L 2/26* (2006.01)
*G07D 11/16* (2019.01)

(52) U.S. Cl.
CPC ............ *A61L 2/10* (2013.01); *A61L 2/26* (2013.01); *G07D 11/16* (2019.01); *A61L 2202/11* (2013.01); *A61L 2202/121* (2013.01); *A61L 2202/14* (2013.01); *A61L 2202/26* (2013.01); *G07D 2211/00* (2013.01)

(58) Field of Classification Search
CPC .......... A61L 2/10; A61L 2/26; A61L 2202/11; A61L 2202/14; A61L 2202/26; A61L 2202/121; G07D 11/16; G07D 2211/00
See application file for complete search history.

(56) References Cited

U.S. PATENT DOCUMENTS

| | | | |
|---|---|---|---|
| 4,866,282 A | 9/1989 | Miripol et al. | |
| 5,120,499 A * | 6/1992 | Baron | A61L 12/063 250/455.11 |
| 6,165,526 A * | 12/2000 | Newman | A23L 3/01 426/248 |
| 6,753,536 B2 * | 6/2004 | Humphreys | A61L 2/04 250/455.11 |
| 8,701,857 B2 * | 4/2014 | Jenrick | G06Q 20/18 235/462.11 |
| 9,235,967 B1 * | 1/2016 | Magee | G06Q 20/401 |
| 10,850,184 B1 * | 12/2020 | Colvin | A61L 2/24 |
| 2004/0099812 A1 * | 5/2004 | Humphreys | A61L 2/04 250/455.11 |
| 2012/0012437 A1 * | 1/2012 | Matsumoto | G07D 1/00 194/342 |

(Continued)

*Primary Examiner* — David A Vanore
(74) *Attorney, Agent, or Firm* — Ostrolenk Faber LLP (57) ABSTRACT

A sanitizing system for sanitizing currency bills at a retailer has a sanitizing apparatus that has an inlet for the insertion therethrough currency bills by a customer, the sanitizing apparatus including a reader for reading the currency bills to establish the total monetary value thereof, and for issuing a receipt to the customer reflecting the total monetary value. A reader located adjacent a cash register at the retailer reads the receipt and accepts the total monetary value as cash tender for merchandize being purchased. A counterfeit detector tests the currency bills and rejects currency bills that do not meet predetermined genuine criteria.

15 Claims, 5 Drawing Sheets

(56) References Cited

U.S. PATENT DOCUMENTS

| | | | | |
|---|---|---|---|---|
| 2013/0045133 A1* | 2/2013 | Maguire | ............... | A61L 2/24 |
| | | | | 422/1 |
| 2022/0044220 A1* | 2/2022 | Herrington | .......... | G06Q 20/206 |
| 2022/0076522 A1* | 3/2022 | Siddiqui | ................ | B42D 25/29 |
| 2022/0257819 A1* | 8/2022 | Pawlowski | ............... | A61L 2/10 |
| 2022/0296755 A1* | 9/2022 | Wurmfeld | ............ | G06K 7/1413 |

* cited by examiner

CURRENCY AND DOCUMENT SANITIZING APPARATUS AND SYSTEM

CROSS-REFERENCE TO RELATED APPLICATION

The present non-provisional patent application is a divisional of prior U.S. patent application Ser. No. 17/319,990, filed May 13, 2021, by Cathy Ann Owen, entitled "CURRENCY AND DOCUMENT SANITIZING APPARATUS AND SYSTEM", which claims the benefit of and priority to U.S. Provisional Patent Application No. 63/073,093, filed Sep. 1, 2020." The contents of each of the patent applications listed above are incorporated in full herein by reference.

BACKGROUND OF THE INVENTION

The present invention generally relates to sanitizing items against disease carrying microbes such as viruses and the like and, more particularly, to an apparatus and method that deploys UV (ultraviolet radiation) for sanitizing, in a manner that enables quick and effective sanitizing of currency bills at point of sale (POS) locations, e.g., retail cash registers, banks and other establishments where money and the like is being exchanged and the need is great for an apparatus/system that provides that function at low cost and at a speed that does not slow the transactions.

It is well established that many forms of infectious disease, such as the common cold, are contracted by and spread to the general public, primarily by direct hand contact and indirectly by way of intermediate materials. The currently on-going Covid-19 pandemic has heightened the need for measures that prevent or at least greatly diminish the spreading of microbes via commercial transactions. It has been discovered that bacteria continue to live on surfaces and objects in the public space that are used and exchanged by numerous individuals within short periods of time. Similarly, disease causing pathogenic agents can live on many different kinds of surfaces and therefore can be a vector for the quick, efficient and expansive spread of various diseases locally, regionally, nationally and internationally within a short span of time.

The prior art is familiar with apparatus and systems for sterilizing commerce media such as legal tender, coins, checks, and any and all other conveyances of monetary exchange used and exchanged by the public, including by using germicidal ultraviolet radiation to kill contaminants such as bacteria and viruses on commerce media.

The prior art has utilized many different forms of sanitization to achieve the purpose of increasing the safety of money bills and the like that are being exchanged in rapid commercial transactions. These methods include the application of sufficient heat and elevated temperatures that kill various microbes such as bacteria, various microorganism molds, fungus and so forth that exist on the surfaces of commercial media. Another approach in the prior art has been to utilize chemical cleansing by effectively "washing" the currency in chemical liquids that provide that function. The third approach, which is being utilized in the present application, is to use radiation and more specifically, ultraviolet radiation.

UV can be subdivided based on its wavelength, as measured in nanometers. UV light is typically divided into three categories including Vacuum UV (10-200 nm); UV-C(Short Wave UV, 200-280 nm); and UV-B (Middle Wave UV, 280-315 nm). The sun and its ultraviolet light are in both near UV and vacuum UV wavelengths, but because of absorption in the atmosphere's ozone layer, 99% of the ultraviolet light that reaches the earth's surface is 315-380 nm (UV-A).

UV is widely used to disinfect drinking water and waste water worldwide, and has been for many years. UV is also extensively used for industrial applications including food and beverage, pharmaceutical and semiconductor manufacturing. Unlike chemical approaches (like chlorine), UV provides rapid, effective inactivation of microorganisms through a physical process. When talking about disinfection in terms of microorganisms, the preferable objective is to achieve a mean reduction of at least 2 log preferably 3 log (or 99.9%).

When bacteria, viruses and protozoa are exposed to UV light, the UV energy destroys the genetic material (DNA) within, eliminating their ability to reproduce and cause infection. This process is known as thymine dimerization. Unable to multiply, the microorganisms are "inactivated," and no longer pose a health risk. The present invention uses the UV-C ultraviolet light as it has been found to be particularly effective to achieve the objectives of the present invention.

In the prior art, U.S. Pat. No. 6,165,526 describes using UV radiation to decontaminate food. The food is inserted into a chamber and exposed to UV radiation for about 15-120 seconds, which is too slow for cash register transactions.

In U.S. Patent Publication No. 2004/0099812, the sanitizing apparatus has a slidable tray that enables insertion of the items to be decontaminated. Both thermal energy and UV-C radiation are deployed to achieve the sanitization objective.

In U.S. Patent Publication No. 2013/0045133, UV radiation and other germicidal methods are used to sterilize currency that is placed into a drawer that is slid into and out of the sterilizing chamber.

In U.S. Pat. No. 5,120,499, UV-C light is used for sanitizing contact lenses where the lenses are exposed to the UV light for a time period of about an hour to two hours.

In U.S. Pat. No. 4,866,282, white blood cells are irradiated with ultraviolet radiation in the 280-320 nm range for about 40 minutes, which is wholly impractical herein. The full contents of the above-identified issued patents and published patent applications are incorporated herein by reference.

SUMMARY OF THE INVENTION

It is an object of the present invention to provide an inexpensive, easy to use and rapidly acting device and system for sanitizing commercial media and the like during active commercial transactions.

Another object of the invention is to provide a device/system for sanitizing currency and the like that can be used at cash registers and which is small sized.

Yet another object of the invention is to provide a commercial media sanitizing system that can be used by customers at commercial establishments where money is being exchanged and also at home.

The foregoing and other objects of the invention are realized with a preferred embodiment in which the sanitizing apparatus comprises a housing defining a sanitizing chamber with an inlet and an outlet for the ingress and egress, respectively, of the currency bills. An intake conveyor conveys the currency bills into the sanitizing chamber into the sanitizing chamber and an outlet conveyor is arranged in the sanitizing chamber along a conveying direction and spaced away from the intake conveyor across a gap therebetween. An upper ultra-violet (UV) lamp is located above the gap and a lower UV light is arranged below the gap. An electrical system causes the upper UV lamp and the lower UV lamp to direct UV light onto an upper surface and a lower surface of the currency bills they are conveyed into the sanitizing chamber and travel across the gap, the UV light being selected to have an intensity to sanitize the currency bills as they pass through the sanitizing apparatus.

Preferably, the apparatus includes reflectors associated respectively with the upper UV lamp and with the lower UV lamp to direct and concentrate the UV light toward the gap, preferably the UV lamps comprise UV-C lamps. The housing has a foot print of not larger than 10×10 inches, for easy location near a cash register. Preferably, the housing comprises an upper housing and a lower housing mated with each other to define the sanitizing chamber and is a stand-alone housing that can be moved and positioned about at a work area near a cash register.

Preferably, the apparatus includes a speed controller for the intake conveyor and an associated selector switch that enables a user to select a speed at which the sheets are conveyed across the gap. The produce UV light having a power in a range of 60-80 mW, a frequency in a range of 260-270 nanometers and UV light at 12 mJ/cm$^2$. The UV lamps and the conveyors are configured to achieve for the currency bills a log 2 and even a log 3 sanitizing effect. Also included are ballasts for producing a high voltage for the UV lamps.

In accordance with another embodiment a sanitizing system for sanitizing currency bills at a retailer is provide which includes a sanitizing apparatus that has an inlet for the insertion therethrough currency bills by a customer, said sanitizing apparatus including a reader for reading the currency bills to establish the total monetary value thereof, and for issuing a receipt to the customer reflecting the total monetary value; and a reader located adjacent a cash register at the retailer, for reading the receipt and accepting the total monetary value as cash tender for merchandize being purchased. At least one counterfeit detector tests the currency bills and rejects currency bills that do not meet predetermined genuine bill criteria. The receipt is coded for one time use. A communication system conveys data from a processor associated with the sanitizing apparatus to a data system associated with the cash register.

Other features and advantages of the present invention will become apparent from the following description of the invention which refers to the accompanying drawings.

DETAILED DESCRIPTION OF PREFERRED EMBODIMENTS OF THE INVENTION

Figure 1:
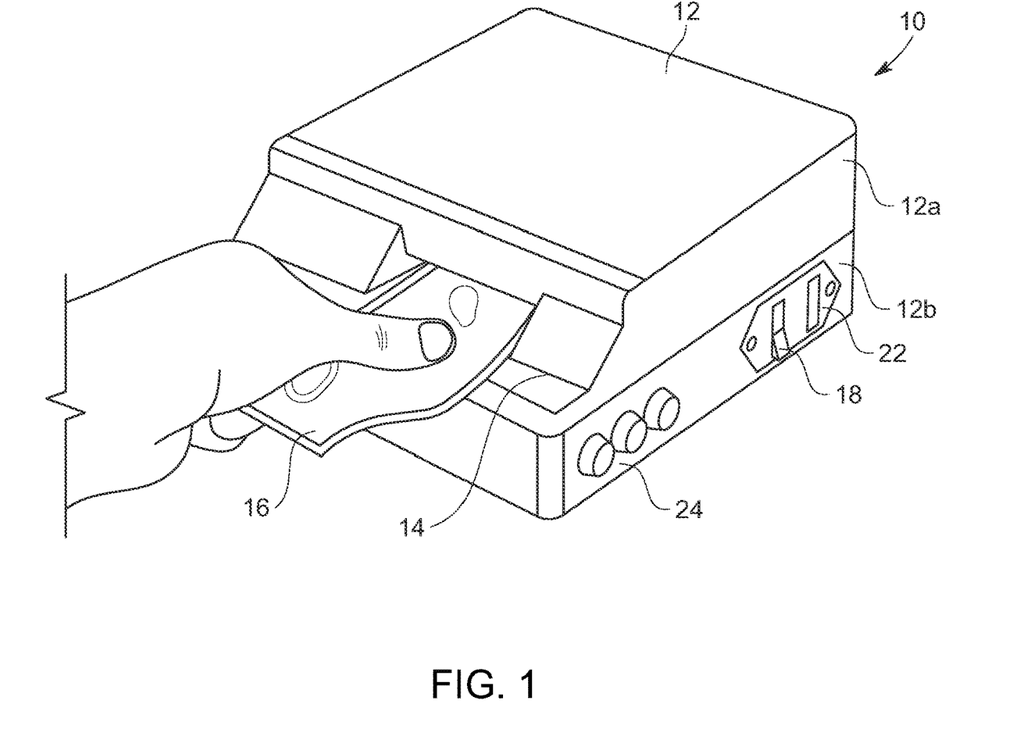
FIG. 1 diagrammatically illustrates a small sized currency sanitizer in accordance with the present invention.

With reference to FIG. 1, a currency sanitizer 10 in accordance with the present invention is small sized and provided as a stand-alone housing 12 that has an upper housing 12a that mates with a bottom housing 12b, defining within the space for the internal mechanisms and circuits needed to effect the sterilizing function. The housing 12 defines an insertion opening 14 for the insertion of currency bills 16, one at a time, into the internal sanitization chamber for being sanitized and thereafter dispensed at the rear, within just one or so seconds after insertion.

The sanitizer 10 measures on the order of less than 10 inches in length and width, preferably less than 8 inches and has a height of less than 5 inches, preferably on the order of 3 inches, whereby it can be easily located next to a cash register, bank teller, etc. and utilized to sanitize currency and the like being passed to the person handling the commercial transaction, greatly reducing the risk of communicating microbes during the transaction. In a proposed embodiment, the foot print of the sanitizer is 7.5×6.5 inches and the height is 3 inches. In another proposed embodiment, the currency bill is fed into the sanitizer widthwise, for speedier travel therethrough.

The housing has a power on/off switch 18 that turns on/off electrical AC power that is provided through an electrical socket 22. Alternatively, internal batteries might be used in future models to provide power to avoid dangling electrical cables.

Figure 2:
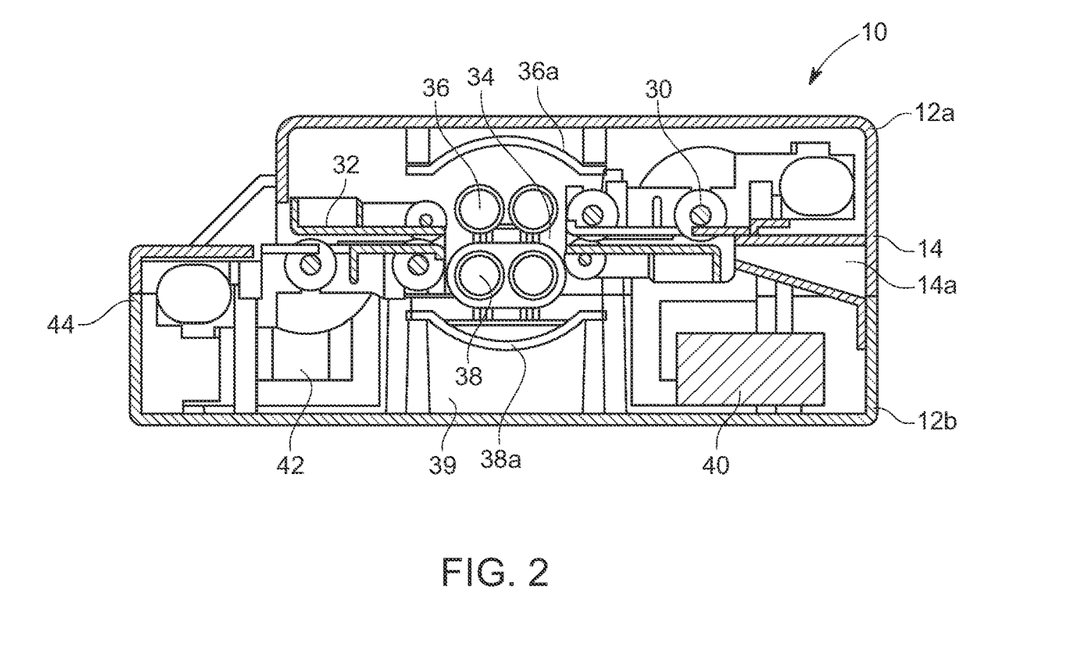
FIG. 2 is a diagram of internal components and a layout for the currency sanitizer of FIG. 1.

Turning to FIG. 2, internal components of the sanitizer 10 include a ramp 14a that provides a path for currency bills 16 to be inserted through the opening 14 into a receiving currency bill driving/moving mechanism 30 that propels the currency bill past a gap 34 which is flanked from above and below by UV-C upper lights 36 and lower UV-C lights 38. The ultraviolet light from the UV-C lamps 36 that is directed upwards is reflected back to the gap 34 by an upper reflector 36a, with a similar functionality being provided by the bottom reflector 38a for the lower UV lamps 38.

As the currency bill 16 travels through the irradiation zone 34, it is subjected to intense UV-C radiation that deactivates the microorganisms on its upper and lower surfaces, so as to render the currency bill 16 safe to handle with glove-free hands. The forward end of the bill 16 is then received by a second driving mechanism 32 and guided to exit through the rear opening 44.

Some of the internal components are powered by a 12 volt DC power supply 40 that receives conventional AC power. The UV lamps 36 and 38 are mounted in respective electrical sockets 39 and are powered by ballasts 42 that produce the high voltage necessary drive these lamps.

Figure 3:
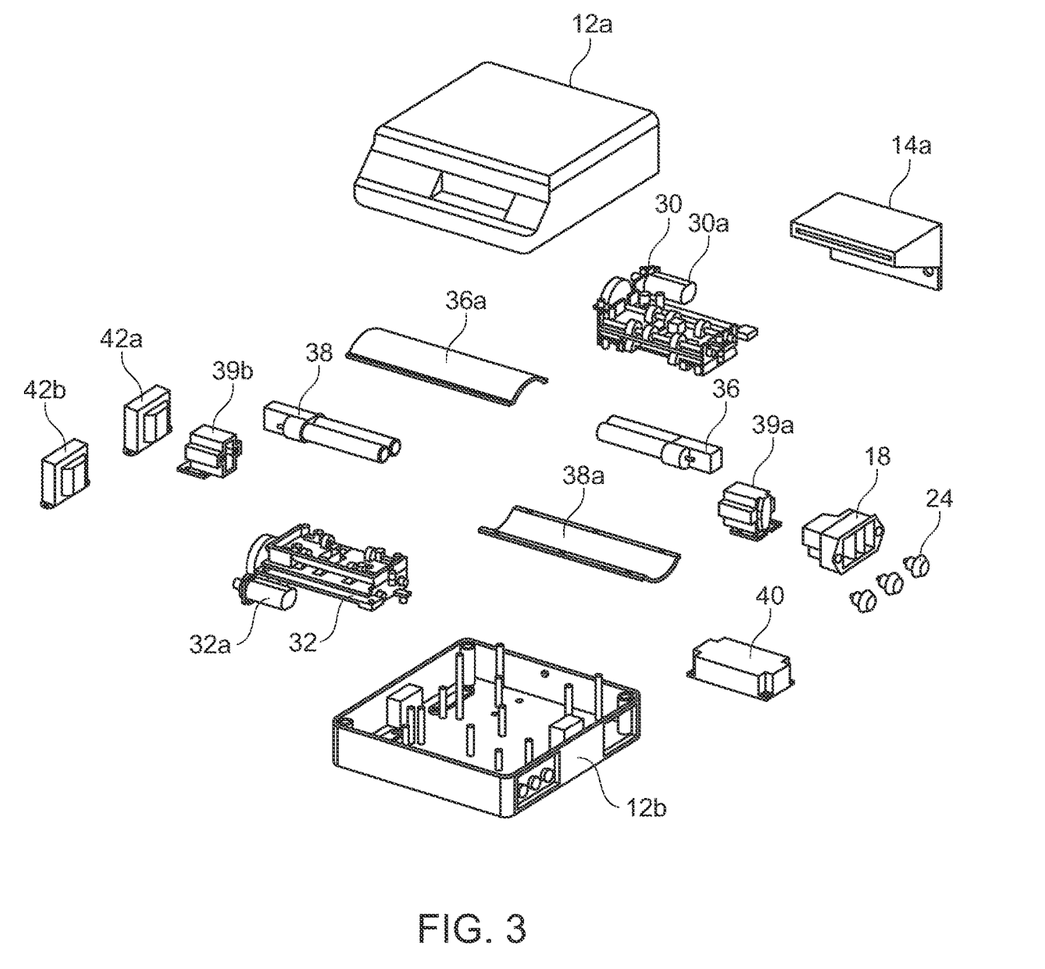
FIG. 3 is an exploded view of internal components and mechanisms of the sanitizer of FIG. 1.

The exploded view in FIG. 3 provides further detail about the internal components including the upper and lower housing halves 12a, 12b that can be produced through 3D printing processes such as by using FDM technology in accordance with manufacturing techniques well known in the art. Thus, the exploded view of FIG. 3 shows the sockets 39a and 39b respectively for the UV bulbs 36 and 38, as well as the upper reflector 36a and the bottom reflector 38a. The power switch and 110 AC socket 18 allow an AC cable (not shown) to be plugged into the sanitizer 10 and enables the power to be turned on/off at will. The general locations for the two ballasts 42a and 42b, one each for the UV-C lamps, are also discernable in FIG. 3, as are further details about the ramp 14a and other components that are used for ramping and transferring the currency bills into and out of the sanitizer 10.

Figure 4:
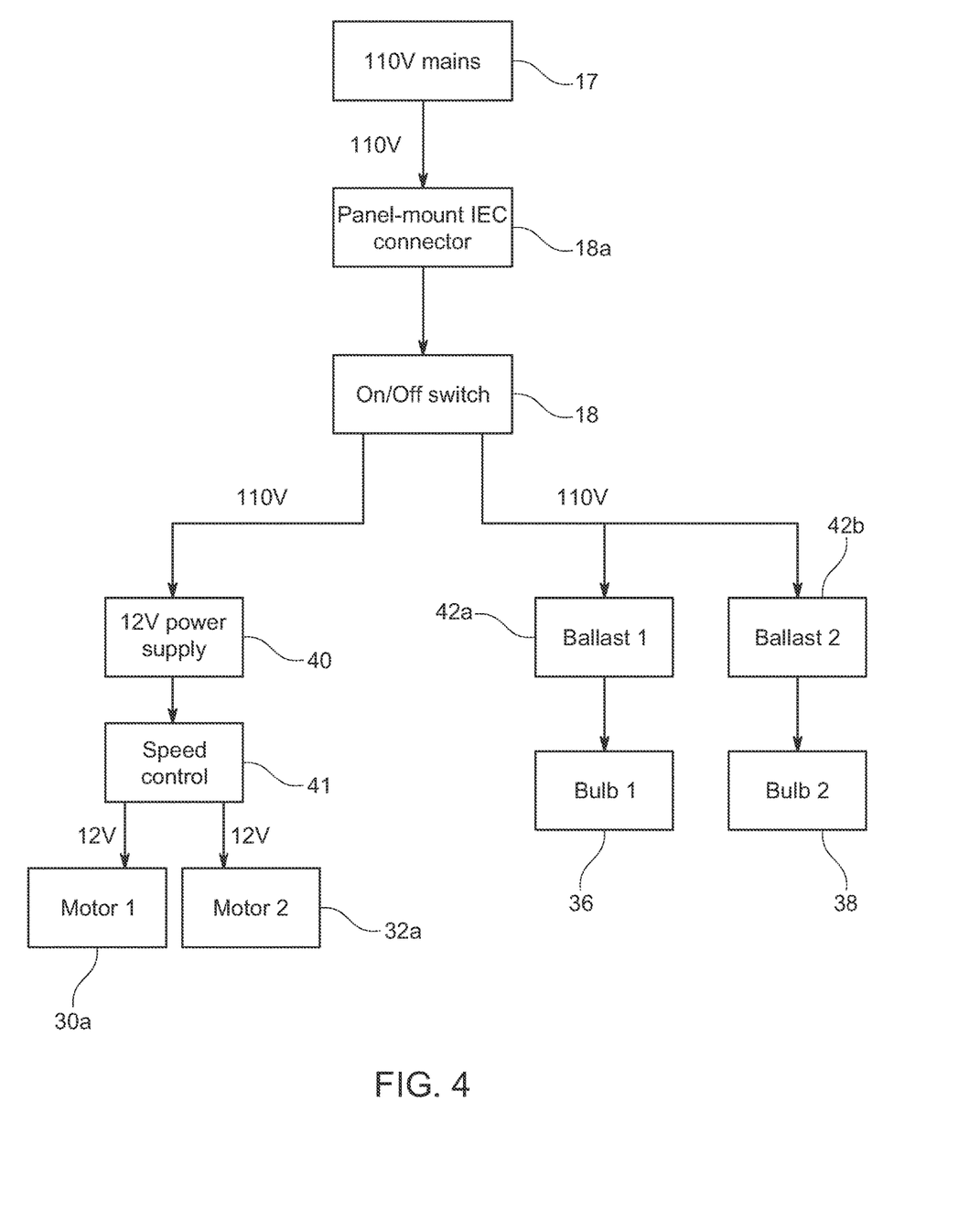
FIG. 4 is an electrical diagram of certain components of the sanitizer of FIG. 1.

Electrically, as shown in FIG. 4, the sanitizer 10 has an AC socket 17 that provides power through a panel mounted IEC connector 18a, which power is directed through the on/off switch 18 providing AC power to the 12 volt DC power supply 40 to drive an optional speed controller that allows the driving speed for the currency bills to be selected, allowing the two motors 30a, 32a to be driven at different selectable speeds. The AC power is also provided to the two ballasts 42a, 42b, which provide the necessary electromotive power to the UVC bulbs 36 and 38.

Figure 5:
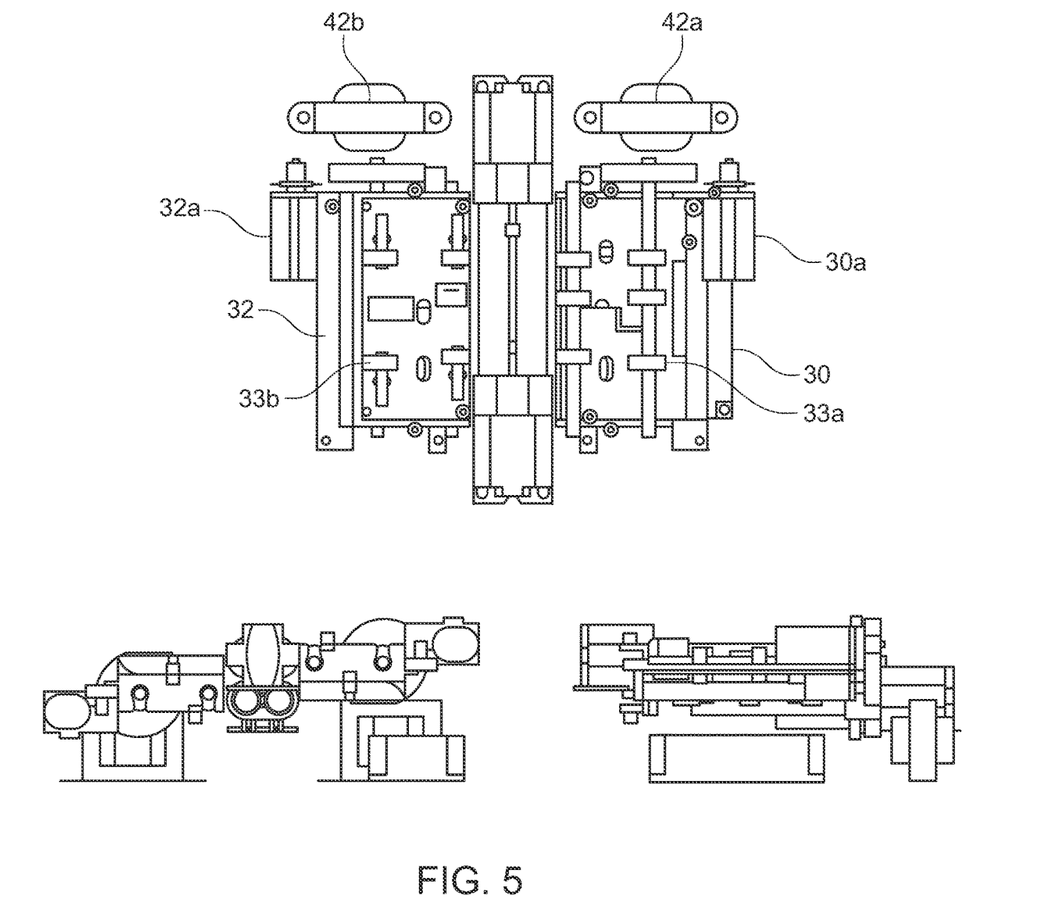
FIG. 5 diagrammatically illustrates a driving mechanism and UV light layout for the sanitizer of the present invention.

Details about the two driving mechanisms that convey the bills through the sanitizer 10 are provided in FIG. 5 and are shown to include the respective motors 30a, 32a as well as their respective rollers 33a, 33b so that when a currency bill 16 is inserted, it is first propelled forward by the first driving mechanism 30 that conveys it past the UV radiation zone 34, between the upper and lower UV bulbs, preferably without any intermediate support structure so that the full intensity of the UV light is concentrated on the currency bill to optimize the cleansing/sanitizing powers of the sanitizer 10b. Although not shown, a small fan can be provided below to create a slight air breeze that maintains the forward edge of the bill horizontal so it does not fall owing to gravity and is thereby properly guided to the second driving mechanism.

As described above, the present invention is able to provide a miniaturized sanitizer that is easily accommodated near cash registers, bank tellers and the like, which can also be used at home to sterilize currency bills, documents and the like. Parenthetically, although not shown, the invention can be modified easily to allow insertion of a tray that holds coins (or bills or documents) and the like that is driven by a single driving mechanism into and then reversibly out of sanitizer 10, conveying the tray through the irradiation zone 34. The concepts of the invention are similarly applicable to an irradiation chamber that is provided with an internal turntable on which are placed multiple bills, so that many bills can be sanitized simultaneously.

Although not limited to being implemented using unique components, the invention may utilize a UV-C LED package output lights as marketed, for example, under the Klaran® brand, which produce between 60 mW-80 mW radiation in a range of 260 nm-270 nm, or similar devices. In an embodiment of the invention, the UV radiation can provide 6 mW/cm$^2$ at the surface of the currency bills and operated at a feed rate of 75 mm per second at an energy intensity of 12 mJ/cm$^2$. Another implementation may use UV-C bulbs that produce 5.1 watts, an energy intensity of approximately 36 mJ/cm$^2$ at a feed rate of 75 mm per second, which UV bulbs are known in the industry as TUV PL-S bulbs. In an embodiment of the invention, the three speeds of the sanitizer 10 can be fixed so that the throughput may be either 1, 2 or 3 seconds, realizing a log 3 sanitizing effect (about 99.9% sanitization level).

In accordance with the invention, the time of disinfection can be set to be on the order of from 2 seconds to 5 seconds per currency bill with a distance traveled by the bill between 6 mm-30 mm at a UV-C power rating of 5 to 10 watts.

In an alternative embodiment of the present invention, the approach to sanitizing bills takes into account the fact that even the expenditure of 2 or 3 seconds per currency bill may cause too much interference at cash registers, particularly when a customer hands over ten bills that might consume about 20 seconds or so to sanitize. To ameliorate even this minor, seconds long, delay, the present invention provides the sanitization system 50 (FIG. 7) that communicates with a central server 90 (FIG. 6) that totally eliminates delay (and actually reduces) the checking out time at cash registers, at bank teller windows and the like.

Figure 7:
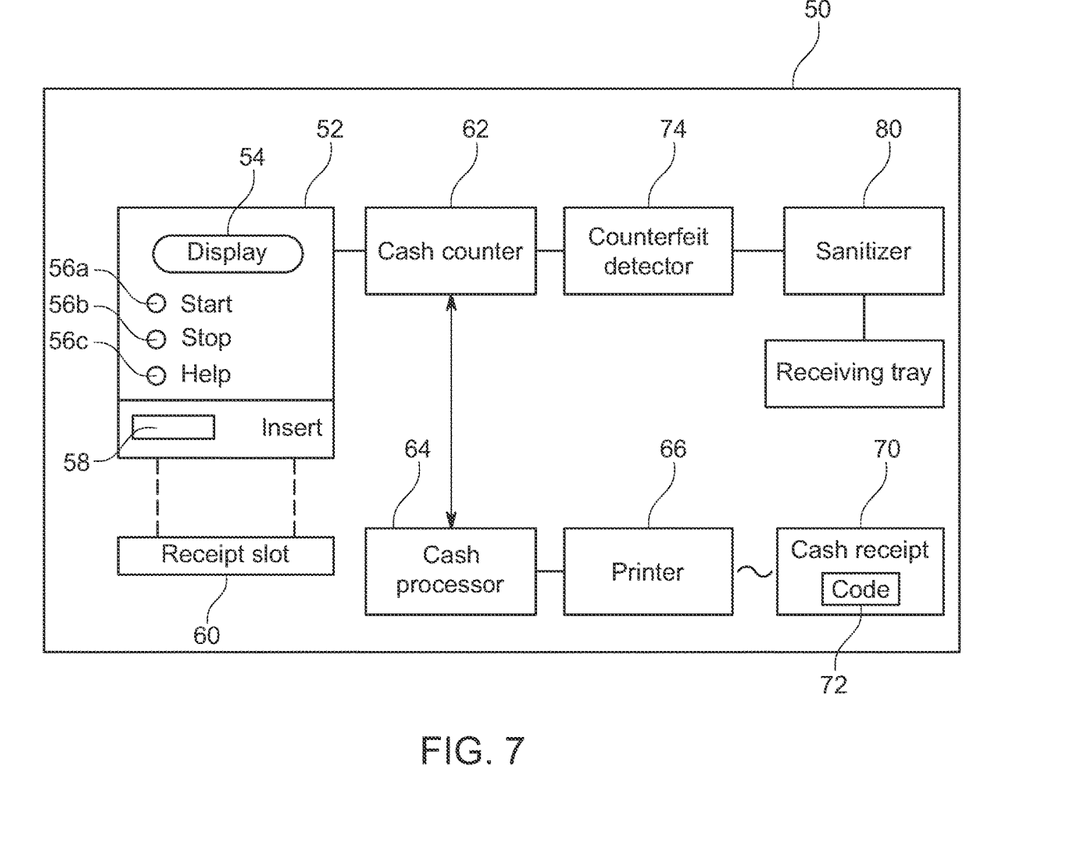
FIG. 7 is a diagram that shows system components of the alternative embodiment of the invention illustrated in FIG. 6.

Referring first to FIG. 7, the sanitizing system 50 is implemented by providing customer interface 52 (which in some embodiments is accessible through a separation wall, similar to the transparent, thick glass separators in banks). Regardless, the customer interface 52 has a display 54 that provides information and operation instructions to the customer. Typically, the customer inserts a currency bill into the currency insertion opening 58, after first pressing the start button 56a. After all the currency bills have been inserted, the stop button 56b is pressed, whereupon the customer will receive for the cash inserted a cash receipt/chit 70 that is provided to the customer through the receipt slot 60.

Internally, the system 50 guides the currency bills inserted through the window 58 to a cash counter 62, per se, known in the field, which counts the amount of the cash as it is inserted and displays the cumulative amount on the customer display window 54. The cash can optionally be guided to a counterfeit detector 74 to identify any counterfeits and inform the customer of such detection (if that functionality is provided).

Most importantly, the bills that are received are guided one by one to sanitizer 80 which can consist of only a single one of the sanitizer embodiment shown in FIG. 1 or a bank of such sanitizers, which quickly sanitize the bill at speeds that might consume less than a second on average for all the bills that are being inserted by customers. The sanitized bills are guided and stored in a receiving tray 82, from which either the business establishment's personnel transfer them to the cash registers throughout the business or simply accepts them in accordance with the establishment procedures.

From the customer's perspective and experience, once the cash is counted by the cash counter 62, which should consume no more than a few seconds, the cash processor 64 receives the information of the total amount of bills that have been inserted and issues the appropriate instructions to printer 66 which then prints out a cash receipt 70 that contains a special code 72 which can be bar or Q-coded, automatically fed from the printer into the receipt slot 60, from which the customer withdraws it. At the cash registers or bank teller stations, the customers need do nothing other than hand the receipt 70 to the cashier or just feed it to a receipt reader.

The cash receipt 70 may be scanned by a reader at the cash register 100 and recorded as cash just handed by the customer, resulting in zero delay at the cashier, and actually a speeded up cash register transaction, given that the cahier is relieved of the task of counting and recounting (and counterfeit checking) actual currency.

Figure 6:
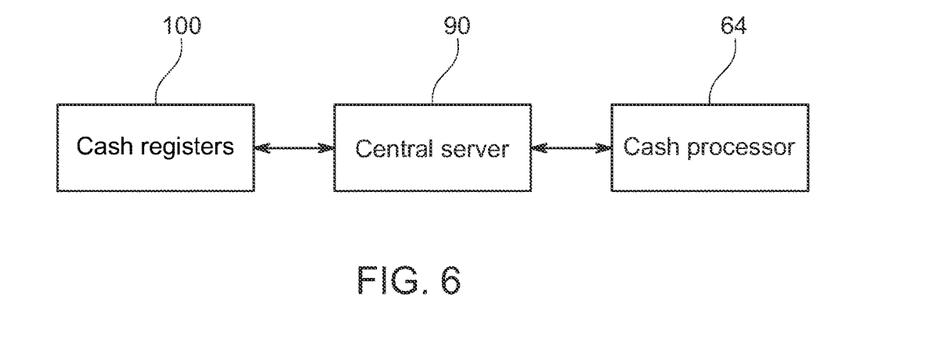
FIG. 6 is a top level diagram of a sanitizing system in accordance with another embodiment of the present invention.

The cash processor 64 shown in both FIGS. 6 and 7 communicates the information about each cash receipt 70 to the central server 90, which in turn is in active communications with the cash registers 100, allowing verification of the authenticity of the receipts 70 and making the printing of fake cash receipts impossible.

In accordance with the present invention, the coding of the cash receipts 70 is extremely reliable as for example by indicating/coding thereon the amount, the date of the generation of the cash receipt and other indicia possibly serial numbers of the bills that have been received, which together make it virtually impossible for unsavory or dishonest people to print their own cash receipts, as they will not have the information to place the right code 72 (which may be date sensitive, currency sensitive, amount sensitive, location sensitive and time sensitive) and therefore, impossible to counterfeit.

While the invention has been described above to receive standard sized U.S. currency, the sanitizer of the present invention can be easily configured to accept documents of different sizes or even items such as credit cards and the like that can be guided into the sanitizer, sanitized and then fed to a cash register that uses the credit card for being swiped through the credit card registration equipment of the cash register where that system is used. Or, credit cards or coins may be fed into and returned to the customers after the sanitization has been effected. Or, the sanitizer may have a turntable on which are placed multiple bills or coins or credit cards and the like, which sequentially and rotatably guides the items through the irradiation zone 34, to cleanse multiple items, dispensing with the need to feed them one by one restricted by the feeding rate of the device.

In an embodiment, the bills are guided in the gap by travelling over a quartz sheet that is UV light transparent and which supports the bills from falling down in the gap. In an embodiment, the bills are guided into the sanitizer by a conventional bill feeder that feeds the bills one by one into the sanitizer. The gap spacing may be on the order of 0.37 inches between the two bill conveyors and the space between the top and bottom bulbs on the order of 0.15 inches. The top of housing is openable to remove bill jams, to replace bulbs and the like. While the sanitizer has been described above for an embodiment where the bills are fed lengthwise into the sanitizer, in actually, embodiments of the invention include arrangements in which the bills are fed in widthwise, shortening the trip duration through the sanitizer by using longer bulbs that span the length of the bills. In different assembly configurations the gaps or distances between drives and from bulb to bill face were as shown below.

| Assembly Concept | Distance between drive mechanisms | Distance from bulb to bill face |
|---|---|---|
| Original (5w) | 1.47 in | 0.189 in |
| Assembly 1 (5w) | 2.84 in | 0.104 in |
| Assembly 2 (18w) | 1.55 in | 0.105 in |
| Assembly 3 (18w) | 1.55 in | 0.105 in |
| Assembly 4 (18w) | 4.60 in | 0.677 in |

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A sanitizing system for sanitizing currency bills at a retailer, comprising:
    a sanitizing apparatus that has an inlet for the insertion therethrough currency bills by a customer, said sanitizing apparatus including a reader for reading the currency bills to establish the total monetary value thereof, and for issuing a receipt to the customer reflecting the total monetary value; and
    a reader located adjacent a cash register at the retailer, for reading the receipt and accepting the total monetary value as cash tender for merchandize being purchased.

2. The sanitizing system of claim 1, wherein the sanitizing system includes at least one counterfeit detector for testing the currency bills and for rejecting currency bills that do not meet predetermined genuine criteria.

3. The sanitizing system of claim 1, wherein the receipt is coded for one time use.

4. The sanitizing system of claim 1, including a communication system that conveys data from a processor associated with the sanitizing apparatus to a data system associated with the cash register.

5. The sanitizing system of claim 1, wherein the sanitizing apparatus comprises:
    a housing defining a sanitizing chamber having an inlet and an outlet for the ingress and egress, respectively, of the currency bills;
    an intake conveyor configured to convey the sheets into the sanitizing chamber;
    an outlet conveyor arranged in the sanitizing chamber along a conveying direction and spaced away from the intake conveyor across a gap therebetween;
    at least one upper ultra-violet (UV) lamp arranged to direct UV light at the gap to strike the currency bills from above and below as the currency bills are conveyed into the sanitizing chamber and travel across the gap, the UV light being selected to have an intensity to sanitize the currency bills while they pass through the gap.

6. The sanitizing system of claim 5, further including reflectors associated respectively with the at least one UV lamp to direct and concentrate the UV light toward the gap.

7. The sanitizing system of claim 5, wherein said at least one UV lamp comprises UV-C lamps.

8. The sanitizing system of claim 5, wherein the housing has a foot print of not larger than 10×10 inches.

9. The sanitizing system of claim 5, including a speed controller for the intake conveyor and an associated selector switch that enables a user to select a speed at which the sheets are conveyed across the gap.

10. The sanitizing system of claim 5, wherein the at least one lamp produces UV light having a power in a range of 60-80 mW and a frequency in a range of 260-270 nanometers.

11. The sanitizing system of claim 5, wherein the at least one UV lamp and the conveyors are configured to achieve for the currency bills at least a 99.9 percent sanitizing effect.

12. The sanitizing system of claim 5, including ballasts for producing a high voltage for the at least one UV lamp.

13. The sanitizing system of claim 5, including motors to drive the conveyors.

14. The sanitizing system of claim 5, including a cooling fan inside the housing.

15. The sanitizing system of claim 5, wherein the housing has a foot print of less than 100 square inches.

* * * * *